United States Patent
Cazzoli et al.

(10) Patent No.: US 12,128,181 B2
(45) Date of Patent: Oct. 29, 2024

(54) VAPORIZER WITH SENSOR

(71) Applicant: JUUL Labs, Inc., San Francisco, CA (US)

(72) Inventors: James R. Cazzoli, San Francisco, CA (US); Maurizio Tarsia, San Carlos, CA (US)

(73) Assignee: JUUL Labs, Inc., San Francisco, CA (US)

( * ) Notice: Subject to any disclaimer, the term of this patent is extended or adjusted under 35 U.S.C. 154(b) by 398 days.

(21) Appl. No.: 17/518,508

(22) Filed: Nov. 3, 2021

(65) Prior Publication Data

US 2022/0053836 A1 Feb. 24, 2022

Related U.S. Application Data

(63) Continuation of application No. PCT/US2020/031457, filed on May 5, 2020.
(Continued)

(51) Int. Cl.
*A24F 40/51* (2020.01)
*A24F 40/10* (2020.01)
(Continued)

(52) U.S. Cl.
CPC ............ *A61M 15/06* (2013.01); *A24F 40/10* (2020.01); *A24F 40/51* (2020.01); *A24F 40/53* (2020.01);
(Continued)

(58) Field of Classification Search
CPC .......... A24F 40/53; A24F 40/10; A24F 40/57; A24F 40/51; A61M 15/06; G06V 40/171; G06V 40/1365; G06V 40/13; G06V 40/10
(Continued)

(56) References Cited

U.S. PATENT DOCUMENTS 9,763,478 B2 9/2017 Cameron et al.
9,770,055 B2 * 9/2017 Cameron ................ A24F 40/30
(Continued)

FOREIGN PATENT DOCUMENTS

CN 206773712 U 12/2017
CN 107568804 A 1/2018
(Continued)

OTHER PUBLICATIONS

PCT/US2020/031457, May 5, 2020, WO/2020/227284.

*Primary Examiner* — Abdullah A Riyami
*Assistant Examiner* — Vladimir Imas
(74) *Attorney, Agent, or Firm* — Mintz Levin Cohn Ferris Glovsky and Popeo, P.C.

(57) ABSTRACT

A vaporization device includes biometric recognition systems. A vaporizer device is provided. The vaporizer device includes a vaporizer body comprising a cartridge receptacle, a heating element, a power source, and a sensor. The vaporizer device further includes a vaporizer cartridge that is selectively coupled to the vaporizer body, the vaporizer cartridge comprising one or more translucent surfaces and a passageway between the sensor and the one or more translucent surfaces. The vaporizer device further includes a controller configured to determine, based on data from the sensor, whether a user is authorized to use the vaporizer device. The controller further configured to provide power to the heating element to generate an aerosol responsive to determining the authorization of the user. Related methods and articles of manufacture are also described.

20 Claims, 14 Drawing Sheets

Related U.S. Application Data

(60) Provisional application No. 62/843,656, filed on May 6, 2019, provisional application No. 62/863,763, filed on Jun. 19, 2019.

(51) Int. Cl.
  *A24F 40/53* (2020.01)
  *A24F 40/57* (2020.01)
  *A61M 15/06* (2006.01)
  *G06V 40/10* (2022.01)
  *G06V 40/12* (2022.01)
  *G06V 40/13* (2022.01)
  *G06V 40/16* (2022.01)

(52) U.S. Cl.
  CPC .............. *A24F 40/57* (2020.01); *G06V 40/10* (2022.01); *G06V 40/13* (2022.01); *G06V 40/1365* (2022.01); *G06V 40/171* (2022.01)

(58) Field of Classification Search
  USPC ........................................................ 131/329
  See application file for complete search history.

(56) References Cited

U.S. PATENT DOCUMENTS

| | | | |
|---|---|---|---|
| 9,888,714 B2* | 2/2018 | Cameron | A24F 40/60 |
| 9,888,723 B2 | 2/2018 | Cameron et al. | |
| 9,936,736 B2* | 4/2018 | Cameron | A24F 40/40 |
| 9,943,111 B2* | 4/2018 | Cameron | A61M 15/06 |
| 9,981,532 B2* | 5/2018 | Blackley | B60H 3/0035 |
| 10,039,325 B2* | 8/2018 | Cameron | G08B 3/10 |
| 10,058,128 B2 | 8/2018 | Cameron et al. | |
| 10,064,432 B2* | 9/2018 | Hawes | A24F 40/60 |
| 10,085,486 B2 | 10/2018 | Cameron | |
| 10,088,464 B2* | 10/2018 | Blackley | G01N 33/0004 |
| 10,212,971 B2* | 2/2019 | Cameron | A24F 40/05 |
| 10,244,791 B2* | 4/2019 | Cameron | B05B 12/12 |
| 10,292,427 B2 | 5/2019 | Cameron et al. | |
| 10,321,711 B2 | 6/2019 | Henry, Jr. et al. | |
| 10,564,655 B2 | 2/2020 | Blackley | |
| 11,350,664 B2* | 6/2022 | Alston | A24F 40/57 |
| 11,399,571 B2* | 8/2022 | Cameron | A24F 40/10 |
| 11,553,730 B2* | 1/2023 | Cameron | B05B 17/0684 |
| 2007/0063816 A1 | 3/2007 | Murakami et al. | |
| 2012/0304990 A1 | 12/2012 | Todd | |
| 2013/0220315 A1 | 8/2013 | Conley et al. | |
| 2014/0060552 A1 | 3/2014 | Cohen | |
| 2015/0122252 A1 | 5/2015 | Frija | |
| 2015/0136158 A1* | 5/2015 | Stevens | A61M 11/042 |
| | | | 131/329 |
| 2015/0181945 A1 | 7/2015 | Tremblay | |
| 2016/0019409 A1 | 1/2016 | Cheng et al. | |
| 2016/0166786 A1 | 6/2016 | Kinzer | |
| 2016/0324217 A1 | 11/2016 | Cameron | |
| 2016/0325055 A1 | 11/2016 | Cameron | |
| 2016/0331022 A1 | 11/2016 | Cameron | |
| 2016/0331023 A1 | 11/2016 | Cameron | |
| 2016/0331024 A1 | 11/2016 | Cameron | |
| 2016/0331025 A1 | 11/2016 | Cameron | |
| 2016/0331026 A1* | 11/2016 | Cameron | A24F 40/50 |
| 2016/0331027 A1 | 11/2016 | Cameron | |
| 2016/0331034 A1* | 11/2016 | Cameron | A61M 15/0003 |
| 2016/0331859 A1 | 11/2016 | Cameron | |
| 2016/0331913 A1 | 11/2016 | Bourque | |
| 2016/0334119 A1 | 11/2016 | Cameron | |
| 2016/0334847 A1 | 11/2016 | Cameron | |
| 2016/0337141 A1 | 11/2016 | Cameron | |
| 2016/0337362 A1* | 11/2016 | Cameron | G06Q 20/3278 |
| 2016/0337444 A1 | 11/2016 | Cameron | |
| 2016/0356751 A1 | 12/2016 | Blackley | |
| 2016/0360789 A1* | 12/2016 | Hawes | H05B 1/0297 |
| 2016/0363570 A1 | 12/2016 | Blackley | |
| 2016/0363572 A1* | 12/2016 | Blackley | G01N 33/15 |
| 2016/0363917 A1 | 12/2016 | Blackley | |
| 2016/0367925 A1 | 12/2016 | Blackley | |
| 2016/0370335 A1 | 12/2016 | Blackley | |
| 2017/0018000 A1 | 1/2017 | Cameron | |
| 2017/0020188 A1 | 1/2017 | Cameron | |
| 2017/0020195 A1 | 1/2017 | Cameron | |
| 2017/0020196 A1 | 1/2017 | Cameron | |
| 2017/0020197 A1 | 1/2017 | Cameron | |
| 2017/0027229 A1 | 2/2017 | Cameron | |
| 2017/0042230 A1 | 2/2017 | Cameron | |
| 2017/0042231 A1 | 2/2017 | Cameron | |
| 2017/0046357 A1 | 2/2017 | Cameron | |
| 2017/0046738 A1 | 2/2017 | Cameron | |
| 2017/0055588 A1 | 3/2017 | Cameron | |
| 2017/0086496 A1 | 3/2017 | Cameron | |
| 2017/0086497 A1 | 3/2017 | Cameron | |
| 2017/0086503 A1 | 3/2017 | Cameron | |
| 2017/0092106 A1 | 3/2017 | Cameron | |
| 2017/0093960 A1 | 3/2017 | Cameron | |
| 2017/0093981 A1 | 3/2017 | Cameron | |
| 2017/0119058 A1 | 5/2017 | Cameron | |
| 2017/0135407 A1 | 5/2017 | Cameron | |
| 2017/0135408 A1 | 5/2017 | Cameron | |
| 2017/0135409 A1 | 5/2017 | Cameron | |
| 2017/0135411 A1 | 5/2017 | Cameron | |
| 2017/0135412 A1 | 5/2017 | Cameron | |
| 2017/0136193 A1* | 5/2017 | Cameron | A24F 40/48 |
| 2017/0136194 A1 | 5/2017 | Cameron | |
| 2017/0136301 A1 | 5/2017 | Cameron | |
| 2017/0181474 A1 | 6/2017 | Cameron | |
| 2017/0181475 A1 | 6/2017 | Cameron | |
| 2017/0185364 A1 | 6/2017 | Cameron | |
| 2017/0196270 A1 | 7/2017 | Vick et al. | |
| 2017/0266397 A1 | 9/2017 | Mayle | |
| 2017/0303590 A1 | 10/2017 | Cameron et al. | |
| 2017/0303593 A1 | 10/2017 | Cameron et al. | |
| 2017/0303594 A1 | 10/2017 | Cameron et al. | |
| 2017/0309091 A1 | 10/2017 | Cameron et al. | |
| 2017/0332702 A1 | 11/2017 | Cameron et al. | |
| 2018/0043114 A1 | 2/2018 | Bowen et al. | |
| 2018/0093054 A1* | 4/2018 | Bowen | A61M 11/042 |
| 2018/0140015 A1 | 5/2018 | Carroll et al. | |
| 2018/0280637 A1 | 10/2018 | Mayle et al. | |
| 2018/0296777 A1 | 10/2018 | Terry et al. | |
| 2018/0310616 A1 | 11/2018 | Clemens et al. | |
| 2019/0158938 A1* | 5/2019 | Bowen | A61M 11/042 |
| 2019/0380388 A1 | 12/2019 | Amorde et al. | |
| 2019/0387796 A1* | 12/2019 | Cohen | A24F 40/30 |
| 2020/0146352 A1* | 5/2020 | Alston | A24F 40/10 |
| 2020/0187565 A1* | 6/2020 | Williams | A61M 11/005 |
| 2020/0352249 A1* | 11/2020 | Achtien | A61M 15/0066 |
| 2021/0345681 A1 | 11/2021 | Cameron | |
| 2022/0053836 A1* | 2/2022 | Cazzoli | A61B 5/0077 |
| 2022/0279846 A1* | 9/2022 | Alston | A24F 40/46 |

FOREIGN PATENT DOCUMENTS

| | | |
|---|---|---|
| CN | 107920589 A | 4/2018 |
| EP | 3342442 A1 | 7/2018 |
| WO | WO-2012138663 A2 | 10/2012 |
| WO | WO-2016172023 A1 | 10/2016 |
| WO | WO-2019173923 A1 | 9/2019 |
| WO | WO-2020006311 A1 | 1/2020 |
| WO | WO-2020023547 A1 | 1/2020 |

* cited by examiner

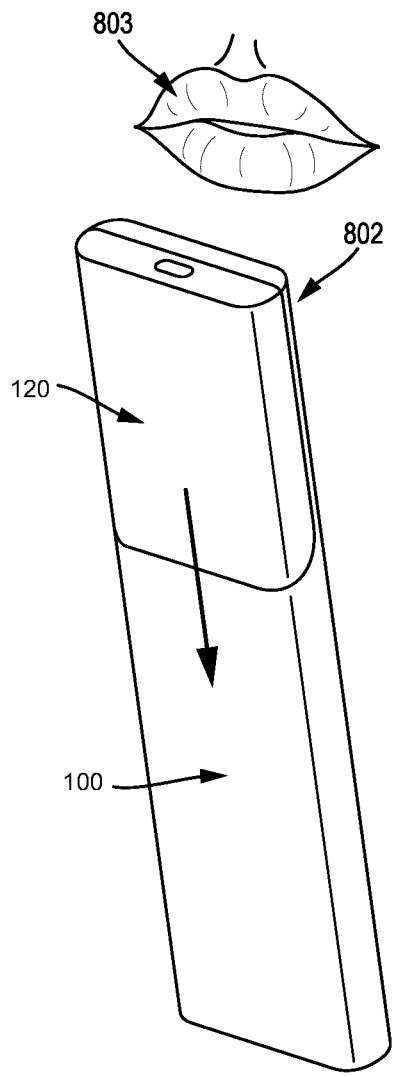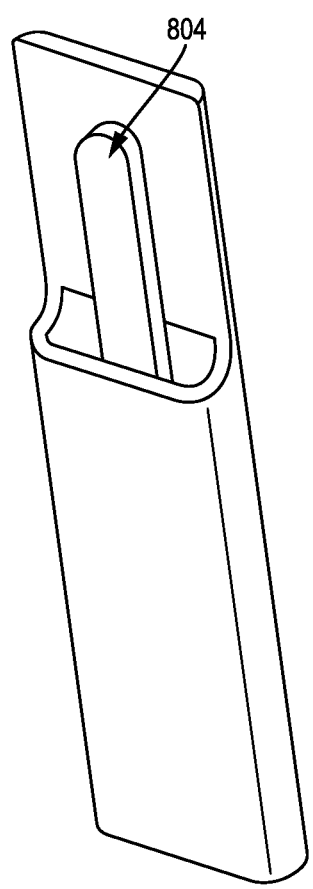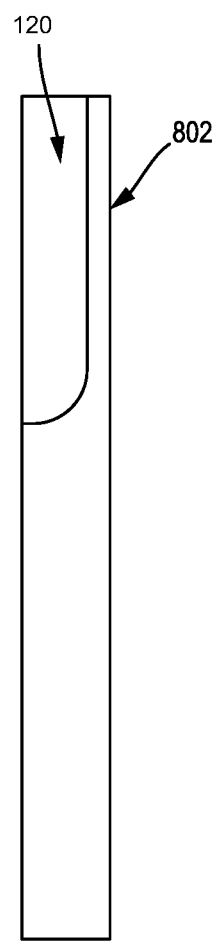
FIG. 8A  FIG. 8B  FIG. 8C

VAPORIZER WITH SENSOR

CROSS-REFERENCE TO RELATED APPLICATIONS

This application is a bypass continuation and claims priority to PCT/US2020/031457, filed on May 5, 2020 and entitled "Vaporizer with Sensor", which claims priority to U.S. Provisional Patent Application Ser. No. 62/843,656 filed on May 6, 2019, entitled "Vaporizer with Sensor", and claims priority to U.S. Provisional Patent Application No. 62/863,763 filed on Jun. 19, 2019, entitled "Vaporizer with Sensor", all of which are hereby incorporated by reference in their entirety to the extent permitted.

TECHNICAL FIELD

The subject matter described herein relates to vaporizer devices, and more particularly, to vaporizer devices with biometric recognition systems.

BACKGROUND

Vaporizer devices, which can also be referred to as vaporizers, electronic vaporizer devices or e-vaporizer devices, can be used for delivery of an aerosol (or "vapor") containing one or more active ingredients by inhalation of the aerosol by a user of the vaporizing device. For example, electronic nicotine delivery systems (ENDS) include a class of vaporizer devices that are battery powered and that may be used to simulate the experience of smoking, but without burning of tobacco or other substances. Vaporizers are gaining increasing popularity both for prescriptive medical use, in delivering medicaments, and for consumption of tobacco, nicotine, and other plant-based materials. Vaporizers, in particular, may be portable, self-contained, and convenient for use.

In use of a vaporizer device, the user inhales an aerosol, commonly called vapor, which may be generated by a heating element that vaporizes (e.g., causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a separate part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

A typical approach by which a vaporizer device generates an inhalable aerosol from a vaporizable material involves heating the vaporizable material in a vaporization chamber (or a heater chamber) to cause the vaporizable material to be converted to the gas (or vapor) phase. A vaporization chamber generally refers to an area or volume in the vaporizer device within which a heat source (e.g., conductive, convective, and/or radiative) causes heating of a vaporizable material to produce a mixture of air and vaporized vaporizable material to form a vapor for inhalation by a user of the vaporization device.

Vaporizers can be controlled by one or more controllers, electronic circuits (e.g., sensors, heating elements), and/or the like on the vaporizer. Vaporizers may also wirelessly communicate with an external controller (e.g., a computing device such as a smartphone).

The systems, apparatuses, and methods described herein address at least these problems and concerns.

SUMMARY

In certain aspects of the current subject matter, challenges associated with unauthorized use of an electronic vaporizer device may be addressed by inclusion of one or more of the features described herein or comparable/equivalent approaches as would be understood by one of ordinary skill in the art. Aspects of the current subject matter relate to identifying lip prints or fingerprints using a vaporizer device with biometric sensing capabilities.

In some variations, one or more of the features described in the following paragraphs may optionally be included in any feasible combination.

The vaporizer device may include a vaporizer body, a vaporizer cartridge, and a controller. The vaporizer body may include a cartridge receptacle, a heating element, a power source, and a sensor. The vaporizer cartridge may be configured to couple to the vaporizer body, and may include one or more translucent surfaces as well as a passageway between the sensor and the one or more translucent surfaces. The controller may be configured to determine, based on data from the sensor, whether a user is authorized to use the vaporizer device and provide power to the heating element to generate an aerosol responsive to determining the authorization of the user.

In some implementations, the vaporizer cartridge further may include a curved surface for improved contact with the user during use of the vaporizer device. The cartridge receptacle may be located on a first side of the vaporizer body, and the sensor may be located on a second side of the device opposite the first side. The cartridge receptacle may be positioned proximate to the vaporizer cartridge on a side of the vaporizer body, thereby allowing for a vaporizer cartridge to be inserted into the cartridge receptacle from the side of the vaporizer body. Consistent with this implementation, the cartridge receptacle may include retention features configured to secure the vaporizer cartridge to the vaporizer body. The cartridge receptacle may be U-shaped, and the sensor may be integrated with the device body proximate to the cartridge receptacle and an end of the vaporizer body.

Additionally, the cartridge receptacle may be configured to receive a cartridge configured to hold a vaporizable material. The cartridge may include a first portion, a second portion, and a third portion spaced apart from the first portion by the second portion and positioned approximately parallel to the first portion. The first portion and the third portion may be positioned approximately perpendicular to the second portion. The first portion may be configured to contain a majority of the vaporizable material, and a wick and a heater of the cartridge may be located within the second portion. An inner surface of the first portion and the third portion may include a retention feature.

In some implementations, the cartridge receptacle and the sensor may be located on a first side of the vaporizer device. The sensor vaporizer device may include a camera configured to capture biometric data (e.g., an image of a lip or finger of the user). The camera may include infrared capabilities configured to detect the lip or finger of the user. The controller may compare a captured biometric data to a previously stored reference biometric data.

In another aspect, the vaporizer cartridge can include two translucent surfaces including a first translucent surface and a second translucent surface, the first translucent surface possibly configured to capture a first portion of a lip print, and the second translucent surface possibly configured to capture a second portion of the lip print.

In some instances the sensor further includes at least one light emitting diode configured to illuminate the passageway. The sensor may be integrated within the vaporizer body proximate to a display module including a biometric sensor configured to recognize a presence of a lip or a finger. The sensor may recognize a presence of a lip of the user by use of a pressure sensor configured to measure a pressure drop. Additionally, the sensor may recognize a presence of a lip or finger of the user by use of an accelerometer configured to determine an orientation of the device, artificial intelligence, or a measurement of total coverage on the one or more translucent surfaces. The data from the sensor may include either a lip print or fingerprint. In some variations, the sensor is part of the vaporizer cartridge. The controller may be configured to read a biometric data of a user. The controller may further be configured to compare the biometric data to reference biometric data. The controller may further be configured to transition the vaporizer device to an active state in which the vaporizer device is capable of vaporizing a vaporizable material, responsive to the biometric data substantially matching the reference biometric data.

In another interrelated aspect of the subject matter, for identifying a user of a vaporizer device based on a biometric recognition system includes reading a lip print or fingerprint from a first user, storing the lip print or fingerprint of the first user, reading a lip print or fingerprint from a second user, storing the lip print or fingerprint of the second user, comparing the lip print or fingerprint of the first user to the lip print or fingerprint of the second user, and powering on the vaporizer device, responsive to the lip print or fingerprint of the first user substantially matching the lip print or fingerprint of the second user. The first user data captured on the vaporizer device may optionally be maintained (e.g., stored) on a personal digital device or an external database. The first user data or second user data may include age information.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to electronic vaporizer devices, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 8A illustrates a vaporizer device with a vaporizer cartridge inserted on one face, with an opposite face having a sensor embedded in the surface;

FIG. 8B illustrates a vaporizer device of FIG. 8A with the vaporizer cartridge removed, showing a visible sensor;

FIG. 8C illustrates a side view of a vaporizer device of FIG. 8A;

When practical, similar reference numbers denote similar structures, features, or elements.

DETAILED DESCRIPTION

Figure 1A:
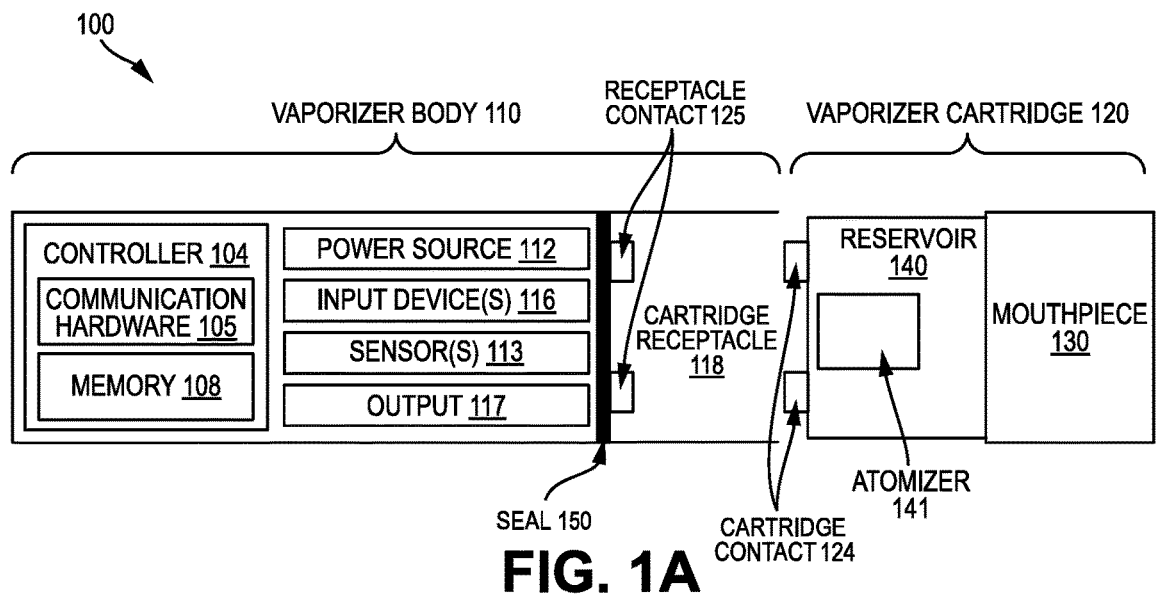
FIG. 1A illustrates a block diagram of a vaporizer consistent with implementations of the current subject matter.

Implementations of the current subject matter include devices relating to vaporizing of one or more materials for inhalation by a user. The term "vaporizer" is used generically in the following description to refer to a vaporizer device. Examples of vaporizers consistent with implementations of the current subject matter include electronic vaporizers, or the like. Such vaporizers are generally portable, hand-held devices that heat a vaporizable material to provide an inhalable dose of the material.

The vaporizable material used with a vaporizer may optionally be provided within a cartridge (e.g., a part of the vaporizer that contains the vaporizable material in a reservoir or other container and that may be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material. In some implementations of the current subject matter, cartridges may be refillable with vaporizable material as necessary, while preserving the electronics, battery, and any sensory components.

In various implementations, a vaporizer may be configured for use with liquid vaporizable material (e.g., a carrier solution in which an active and/or inactive ingredient(s) are suspended or held in solution or a neat liquid form of the vaporizable material itself). A liquid vaporizable material may likewise be capable of being completely vaporized or may include some part of the liquid material that remains after all of the material suitable for inhalation has been consumed.

In various implementations, a vaporizer may be configured to prevent unauthorized usage of the vaporizer. Previous attempts to prevent unauthorized usage of a vaporizer using identification techniques may be improved using one or more of the approaches described herein. While age-verification may be performed when a vaporizer is purchased, such approaches do not prevent the vaporizer from later being given to an unauthorized user such as, for example, an under-age user, a non-smoker, and/or the like. Existing techniques for preventing use by unauthorized users may include requiring a vaporizer to perform periodic synchronizations with a computing device (e.g., a smartphone, a personal computer, and/or the like) via, for example, Bluetooth low energy (BLE) or another short range wireless communication protocol. In the absence of synchronization, the vaporizer may become disabled and incapable of vaporizing a vaporizable material. However, this requirement for periodic synchronization with a computing device may be inconvenient and give rise to user friction.

Cheiloscopy refers to a forensic investigation technique in which individual identities are determined based on lip traces. Due to the uniqueness and permanence of the characteristics of lips, lip prints may be akin to fingerprints in that lip prints are unique to each individual.

Various biometric sensors including, for example, optical sensors, capacitive sensors, and/or ultrasonic sensors, may be used to capture lip print and/or fingerprint information. For example, an optical sensor with light-emitting diodes (LEDs) may be implemented using an acrylic inner cover (e.g., dead-front face) to improve the detection of the grooves and ridges of a lip print or a fingerprint. Alternatively, ultrasonic sensors may be used in order to achieve better performance against moisture and grease (e.g., saliva, lipstick, and/or the like). Meanwhile, capacitive sensors may use electrical current instead of light in order to generate one or more images of the grooves and ridges forming current lip print and/or a fingerprint. Since the distance to the finger and/or lip alters capacitance, a finger ridge may result in a different voltage output than a finger and/or lip valley. One advantage of a capacitive sensor is that it requires a real lip print or fingerprint-type shape, rather than the pattern of light and dark that makes up the visual impression of a lip print or fingerprint. This may make an authentication or an identification system more difficult to circumvent.

In some implementations of the current subject matter, one or more biometric sensors may be implemented behind a display. For example, a display may be implemented with a capacitive sensor, an optical sensor, and/or an ultrasonic sensor underneath the display. A lip print and/or a fingerprint may be detected and differentiated depending on where the user contacts the display.

In some implementations of the current subject matter, a vaporizer may include one or more of biometric sensors including, for example, optical sensors, capacitive sensors, ultrasonic sensors, and/or the like. The one or more biometric sensors may be located within a vaporizer body (e.g., vaporizer body 110) and/or a vaporizer cartridge (e.g., vaporizer cartridge 120) configured to be coupled with the vaporizer body. The one or more biometric sensors may be configured to capture biometric data including, for example, lip prints, fingerprints, and/or the like. The biometric data captured at the vaporizer for example, by the one or more biometric sensors, may be used to control access to the vaporizer For example, in order to activate the vaporizer, the biometric data captured by the one or more biometric sensors may be required to match reference biometric data for an authorized user. Activating the vaporizer may include transitioning the vaporizer from an inactive state in which the vaporizer is incapable of vaporizing a vaporizable material to an active state in which the vaporizer is capable of vaporizing the vaporizable material. In the event the biometric data captured at the vaporizer fails to match the reference biometric data of an authorized user, the vaporizer may remain in the inactive state. Accordingly, an unauthorized user whose biometric data does not match the reference biometric data of an authorized user may be thwarted from using the vaporizer at least because the vaporizer may be incapable of vaporizing the vaporizable material when the unauthorized user attempts to use the vaporizer.

In the example of optical capture of a lip print and/or a fingerprint, a user may press his or her lip or finger on a translucent surface that is part of or otherwise associated with the vaporizer. In some implementations, the translucent surface may be formed at least partly from a molded polycarbonate substance. Two or more translucent surfaces may optionally be included, for example in an implementation of a cheiloscopic approach, to enable prints of the top and bottom lips to be captured concurrently (in other words, during a single action of the user placing the sensor part of the vaporizer between his or her lips). Capture of an image may be triggered by one or more approaches, possibly including but not limited to detection of a pressure change (e.g., a pressure change caused by a user inhaling or blowing into a mouthpiece of the vaporizer) by a pressure sensor that is part of or otherwise associated with the vaporizer, detection of an orientation change or movement by an accelerometer that is part of or otherwise associated with the vaporizer, measurement of total lip or finger coverage on one or more sensors (e.g., the translucent surface or surfaces described in the optical capture example above), by other analytical approaches (e.g., application of machine learning or artificial intelligence or the like), etc. The lip print or fingerprint image may transfer to the sensor through a corridor within the interior of the vaporizer and/or the vaporizer cartridge. Alternatively, the sensor may be positioned proximate to an exterior surface of the vaporizer and/or the vaporizer cartridge.

In a preferred embodiment, the corridor through which the image of the lip print or fingerprint is transferred may be a light piping, used in the vaporizer and/or mouthpiece for transporting or distributing natural or artificial light. The transfer of the lip print or fingerprint may be aided by one or more light emitting diodes or use of a camera with infrared capabilities. After the image capture of the lip print and/or fingerprint, identification of an individual may be determined based on the image data. Once a second user attempts to use the vaporizer, a second image may be similarly be captured. A comparison of the biometric data to the reference biometric data may occur to determine a threshold matching value comparing the lip print or fingerprint of the first user to the reference biometric data. Powering on of the vaporizer may be responsive to, or conditioned on, the threshold matching value being satisfied.

It will be understood from the disclosure herein that optical sensors are not the only option for capturing biometric data. For example, in place of a translucent part covering an optical sensor, a capacitive sensor or a surface incorporating capacitive sensing features may be used. Also as noted above, ultrasonic sensors may optionally be incorporated.

Additional safety features for further authorization and/or authentication subsequent to matching a lip print and/or a fingerprint matching may include age verification of a user of the vaporizer. This age information associated with the user may be automatically stored locally on the device, or retrieved, for example, from an external database by a computing device coupled with the vaporizer (e.g., as part of a vaporizer system including the vaporizer and the computing device). For example, after identifying the user's identity based on the captured lip print and/or fingerprint, the vaporizer may retrieve age information from an external database (e.g., a DMV server) by the computing device (e.g., a smart phone running an application associated with the vaporizer).

In some implementations, vapor production may commence upon determining that a lip print and/or a fingerprint captured by the vaporizer match a reference lip print and/or a reference fingerprint of an authorized user. For example, the user may be authorized for using the vaporizer subsequent to a successful age verification. The quantity of vapor generated by the vaporizer may be determined based on one or more prescriptions and/or preferences associated with the authorized user. Contrastingly, the vaporizer may remain, or optionally become, inoperative (e.g., incapable of generating vapor) if the lip print and/or the fingerprint captured by the vaporizer fail to match a reference lip print and/or a reference fingerprint of an authorized user. It should be appreciated that the vaporizer may be in deactivated by disabling one or more components of the vaporizer including, for example, a heater element, a pressure sensor, and/or the like.

Figure 1B:
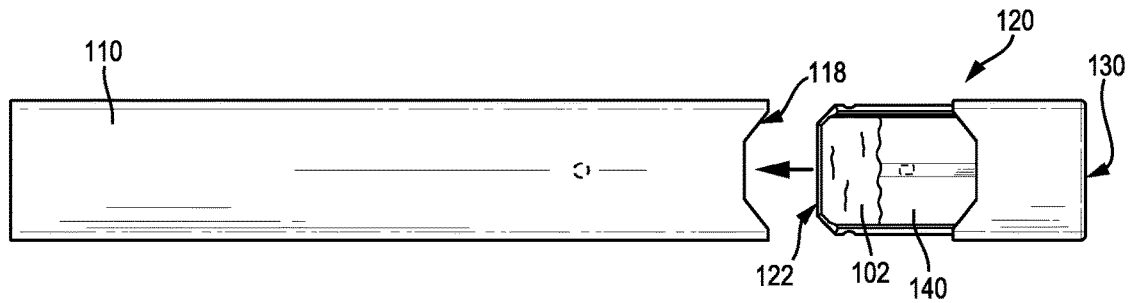
FIG. 1B illustrates a front view of an embodiment of the vaporizer of FIG. 1A showing a cartridge separated from a vaporizer device body.

FIG. 1A depicts a block diagram illustrating an example of a vaporizer 100 consistent with implementations of the current subject matter. FIG. 1B depicts a top planar view of an example of the vaporizer body 110 and the vaporizer cartridge 120. Referring to FIG. 1A, the vaporizer 100 typically includes a power source 112 (such as a battery which may be a rechargeable battery), and a controller 104 (e.g., a processor, circuitry, etc. capable of executing logic) for controlling delivery of heat to an atomizer 141 to cause a vaporizable material 102 to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer 141 in which a wicking element (also referred to herein as a wick (not shown in FIG. 1A), which can include any material capable of causing fluid motion by capillary pressure) conveys an amount of a liquid vaporizable material to a part of the atomizer that includes a heating element (also not shown in FIG. 1A). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes a resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 130 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 130 for inhalation by a user).

Activation of the heating element may be caused by automatic detection of the puff based on one or more of signals generated by one or more sensors 113. As such, the one or more sensors 113 may include pressure sensors disposed along and/or proximate to the airflow path and configured to detect an absolute pressure and/or a pressure relative to an ambient pressure. Alternatively and/or additionally, the one or more sensors 113 may include motion sensors, flow sensors, and/or biometric sensors. In some implementations of the current subject matter, the biometric sensors may be configured to detect contact between a user and the vaporizer 100 as well as capture biometric data (e.g., a lip print and/or fingerprint) associated with the user. Activation of the heating element may be based on the biometric data matching biometric data of an authorized data. Instead of and/or in addition to the one or more sensors 113, a puff (or an imminent puff) may also be detected based on other user interactions with the vaporizer 100 including, for example, contact with one or more input devices 116 (e.g., buttons or other tactile control devices of the vaporizer 100), signals from a computing device coupled with the vaporizer 100 and/or the like.

As alluded to in the previous paragraph, the vaporizer 100 may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 150 to separate an airflow path from other parts of the vaporizer. The seal 150, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 150 may also separate parts of one or more electrical connections between a vaporizer body 110 and a vaporizer cartridge 120. Such arrangements of a seal 150 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 150 can also result in a user inhaling air that has passed over parts of the vaporizer device containing or constructed of materials that may not be desirable to be inhaled.

Referring again to FIG. 1A, the vaporizer 100 may be configured to couple with a vaporizer cartridge 120. For example, as shown in FIG. 1A, the vaporizer 100 may include a cartridge receptacle 118 configured to receive the vaporizer cartridge 120. Moreover, as shown in FIG. 1A, the vaporizer cartridge 120 may include a reservoir 140 containing a liquid vaporizable material 102 and a mouthpiece 130 for delivering an inhalable dose to a user. The vaporizer cartridge 120 can include an atomizer 141 having a wicking element and a heating element, or alternatively, one or both of the wicking element and the heating element can be part of the vaporizer body 110. In implementations in which any part of the atomizer 141 (e.g., heating element and/or wicking element) is part of the vaporizer body 110, the vaporizer 100 can be configured to supply liquid vaporizer material 102 from the reservoir 140 in the vaporizer cartridge 120 to the portions of the atomizer 141 included in the vaporizer body 110.

In vaporizers in which the power source 112 is part of the vaporizer body 110 and a heating element is disposed in the vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source 112, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect. In other words, one or more circuits necessary for operation of the vaporizer can be completed by insertion of a vaporizer cartridge 120 in the cartridge receptacle 118.

In one example of an attachment structure for coupling a vaporizer cartridge 120 to the vaporizer body 110, the vaporizer body 110 includes a detent (e.g., a dimple, protrusion, etc.) protruding inwardly from an inner surface the cartridge receptacle 118. One or more exterior surfaces of the vaporizer cartridge 120 can include corresponding recesses (not shown in FIG. 1A) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110), the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

FIG. 1B illustrates an embodiment of the vaporizer body 110 having a cartridge receptacle 118 into which the cartridge 120 may be releasably inserted. FIG. 1B shows a top view of the vaporization device 100 illustrating the cartridge being positioned for insertion into the vaporizer device body 110. When a user puffs on the vaporization device 100, air may pass between an outer surface of the cartridge 120 and an inner surface of a cartridge receptacle 118 on the vaporizer device body 110. Air can then be drawn into an insertable end 122 of the cartridge, through the vaporization chamber that includes or contains the heating element and wick, and out through an outlet of the mouthpiece 130 for delivery of the inhalable aerosol to a user. The reservoir 140 of the cartridge 120 may be formed in whole or in part from translucent material such that a level of vaporizable material 102 is visible along the cartridge 120.

Figure 2A:
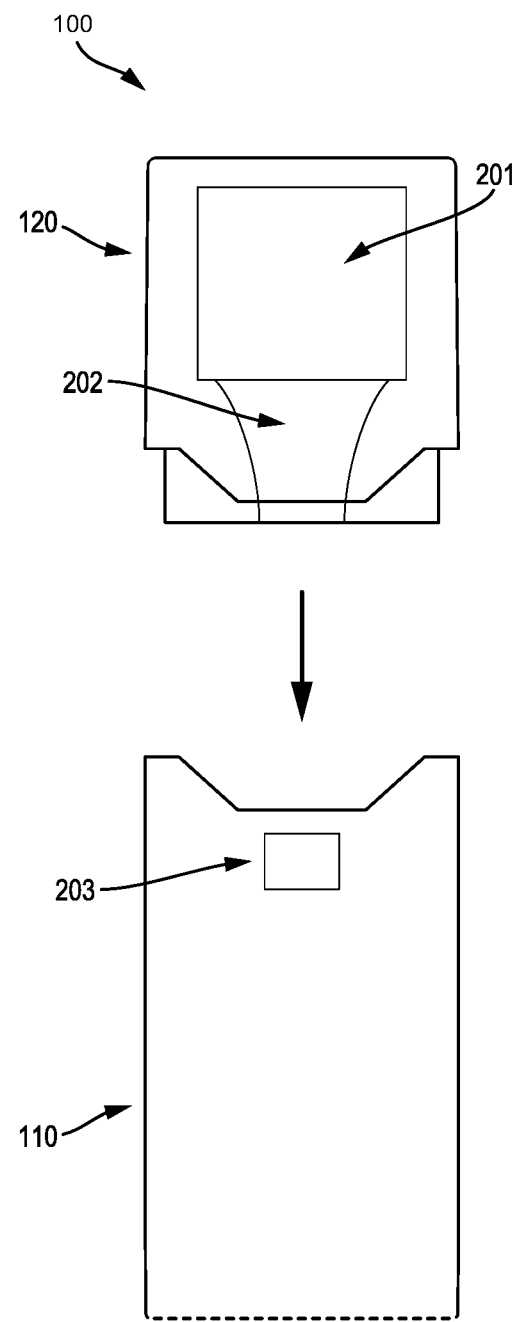
FIG. 2A illustrates a perspective drawing of a vaporizer device, consistent with implementations of the current subject matter.

FIG. 2A illustrates a front view of the vaporizer device 100 having a disconnected cartridge 120 having a translucent surface 201 that a lip or finger would be pressed against for lip print or fingerprint capture. For example, when a user attempts to inhale on the mouthpiece 130 of the cartridge 120, a portion of the user's finger and/or lip may contact the translucent surface 201. As shown in the example of FIG. 2A, the cartridge 120 includes a light pipe 202 extending from the translucent surface 201 to a camera module 203 of the vaporizer body 110 when the cartridge 120 is coupled to the vaporizer body 110. The camera module 203 may capture the lip print or the fingerprint of the user in response to the user's finger and/or lip contacting the translucent surface 201.

Figure 2B:
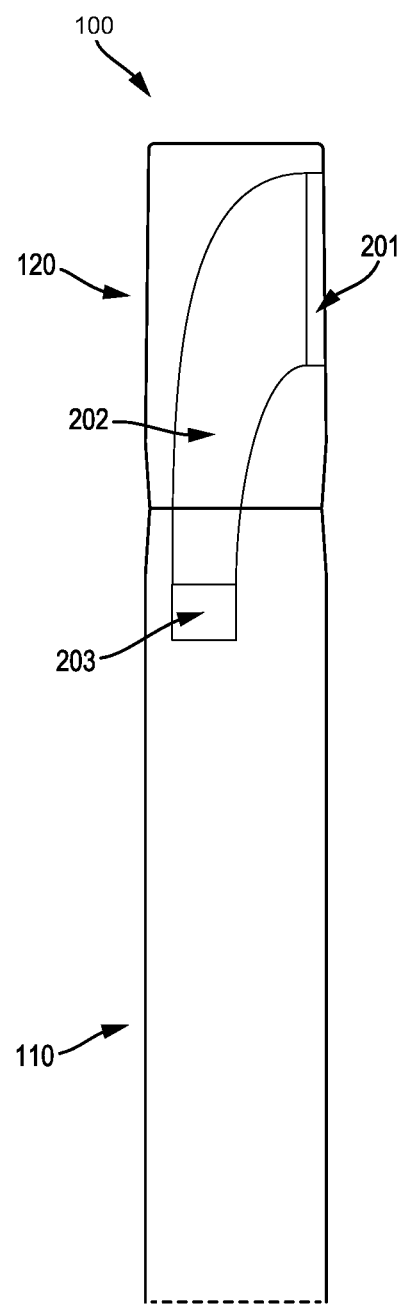
FIG. 2B illustrates a side view of a vaporizer device of FIG. 2A.

FIG. 2B illustrates a side view of the vaporizer device 100 having the vaporizer cartridge 120 coupled to the vaporizer body 110. As shown in FIG. 2B, the translucent surface 201 that a lip or a finger may be pressed against for a lip print or a fingerprint capture is positioned proximate to an exterior surface of the vaporizer cartridge 120. Once a lip or a fingerprint of the user triggers image capture, the camera module 203 may transmit light through the light pipe 202 to the translucent surface 201 to capture an image of the lip print or fingerprint contacting the translucent surface 201. In response to capturing the image, a processor (e.g., controller 104) may process the image for identification, authorization, and/or authentication of the user.

Figure 2C:
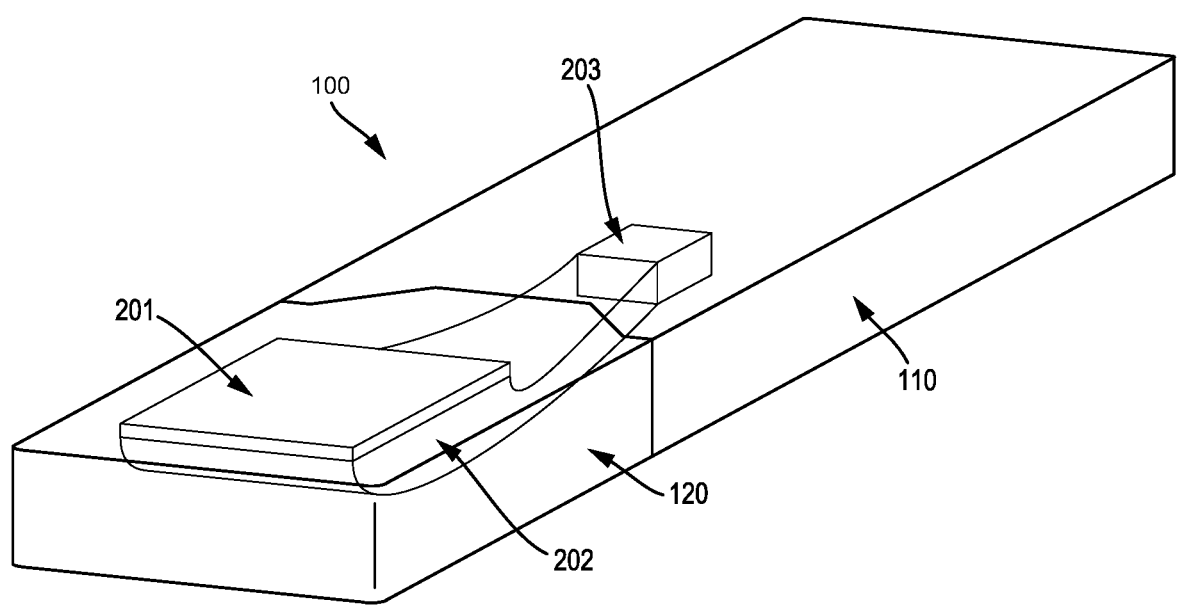
FIG. 2C illustrates a perspective view of a vaporizer device of FIG. 2A.

FIG. 2C illustrates an angled view of the vaporizer device 100. As shown in FIG. 2C, the light pipe 202 extends from the cartridge 120 to the camera module 203 of the vaporizer body 110. In some aspects, the camera module 203 may be located within the vaporizer cartridge 120.

Figure 3:
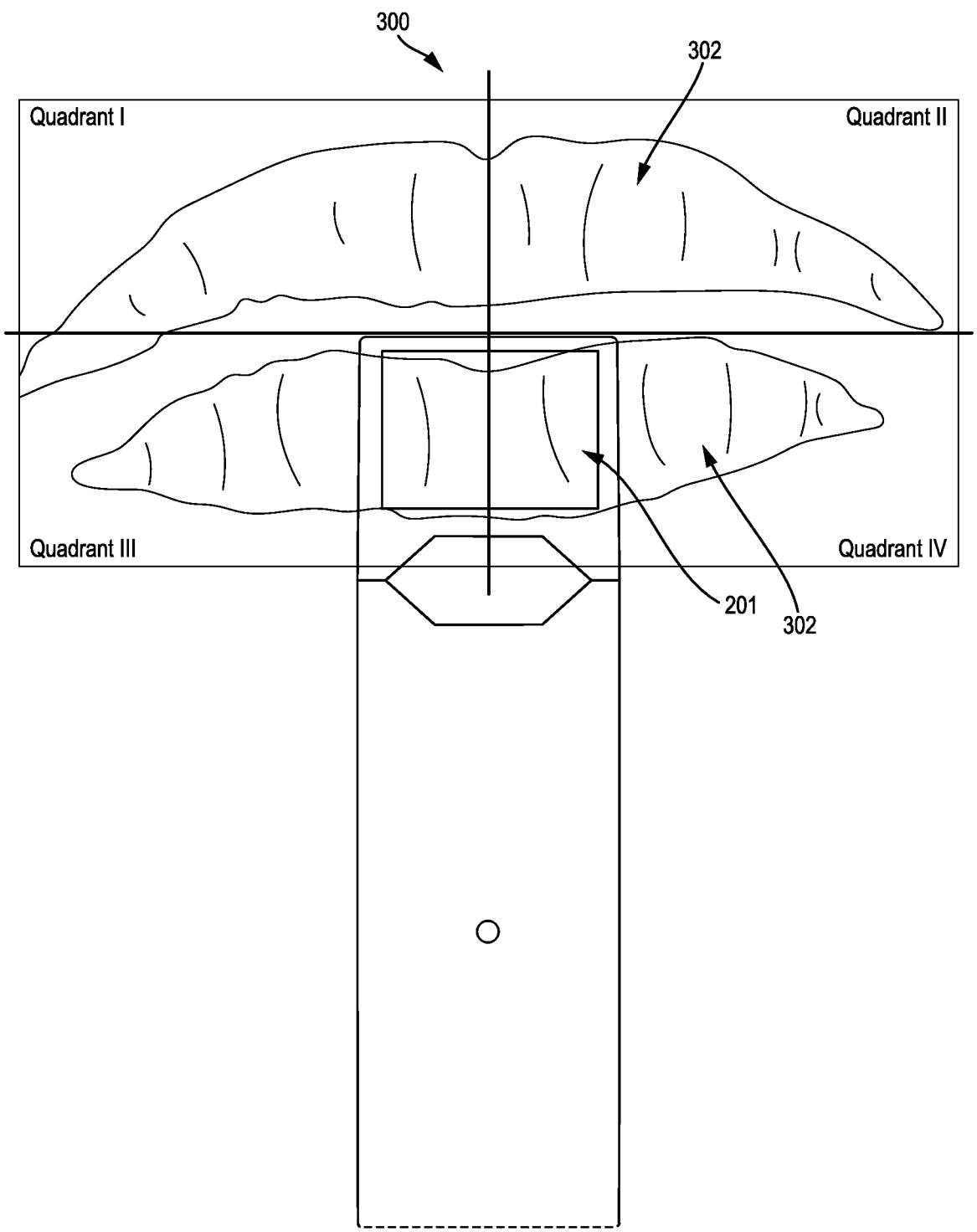
FIG. 3 illustrates a perspective view of a typical placement of lips on a vaporizer device with cheiloscopic recognition capabilities.

FIG. 3 illustrates a full lip print of lips 302 including four quadrants 300, which can be captured and stored locally, or on an external device for further analysis and threshold matching. FIG. 3 further illustrates a front view of a typical, centered placement of lips 302 on a mouthpiece (e.g., mouthpiece 130) of the vaporizer cartridge 120 with the translucent surface 201. As shown, a portion of the lips 302 my contact the translucent surface 201. A sensor (e.g., the camera module 203) may detect the biometric data (e.g., lip print or fingerprint) in response to a coverage on the translucent surface 201 exceeding a threshold value. The portion of the lips 302 or a portion of a finger (not shown) contacting the translucent surface 201 may be sufficient for identification, authentication, and/or authorization of the user. In some aspects, the portion of the lips 302 may satisfy a threshold surface area or a threshold portion of one or more quadrants 300 in order to authorize activation of the vaporizer 100 or capture of the biometric data.

Figure 4:
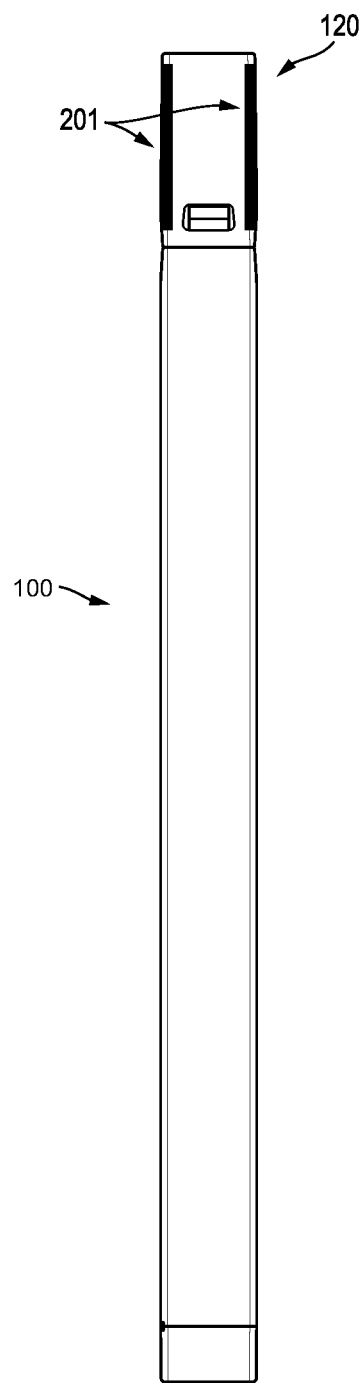
FIG. 4 illustrates a side view of a vaporizer device with two translucent surfaces on the front and back portions of a mouthpiece.

FIG. 4 illustrates a side view of the vaporizer device 100 with the translucent surface 201 on both a front side and a back side of the cartridge 120, providing a capability to capture lip prints for both top and bottom lips. While translucent surfaces 201 are shown in certain locations of the cartridge 120 in the example of FIG. 4, the translucent surfaces 201 may be located in different locations of the cartridge 120 or may be located on the vaporizer body 110.

Figure 5A:
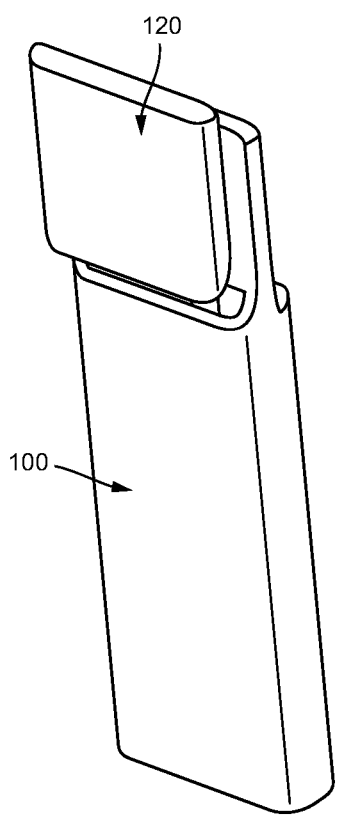
FIG. 5A illustrates a vaporizer device with a vaporizer cartridge inserted on one face, with an opposite face that has curvature for improved lip contact.

FIG. 5A illustrates a vaporizer 100 with the vaporizer cartridge 120 inserted on one side of the vaporizer 100. As shown, the cartridge 120 couples to the vaporizer device 100 at a superior end of the vaporizer 100.

Figure 5B:
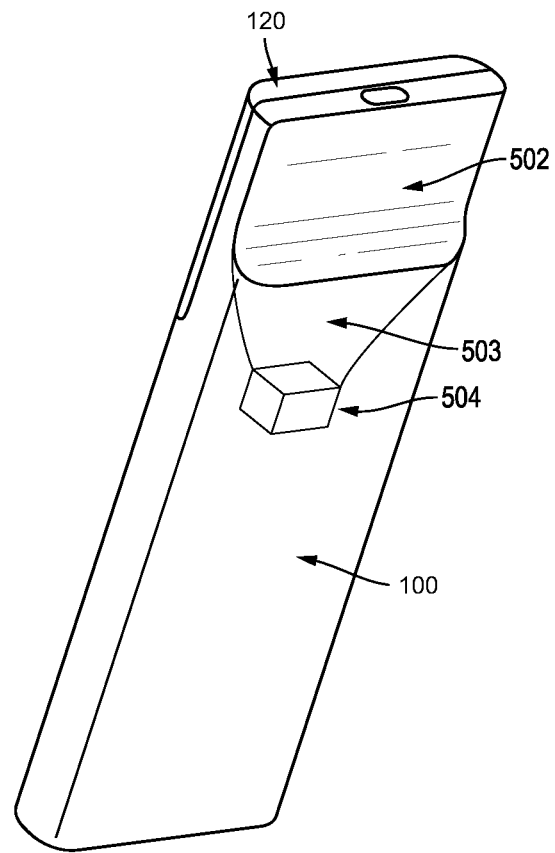
FIG. 5B illustrates a perspective view of a vaporizer device of FIG. 5A.

FIG. 5B illustrates a perspective view of the example of the vaporizer 100 shown in FIG. 5A with the vaporizer cartridge 120 coupled to the vaporizer body 110. As shown, the vaporizer 100 includes a curved surface 502 for improved contact with the user's lip and/or finger on the curved surface 502. The curved surface 502 may include a translucent surface (e.g., translucent surface 201) configured to facilitate capture of a lip print and/or a fingerprint of a user contacting the curved surface 502. As further shown in FIG. 5B, light piping 503 may extend from the curved surface 502 and may be used to direct light to a sensor 504 (e.g., optical, capacitive, ultrasonic, or the like) for the sensor 504 to capture better resolution images of lip prints and/or fingerprints contacting the curved surface 502. The lip prints and/or fingerprints captured by the sensor 504 may be processed by a processor of the vaporizer device 100 (e.g., controller 104) for user identification, authentication, and/or authorization.

Figure 6:
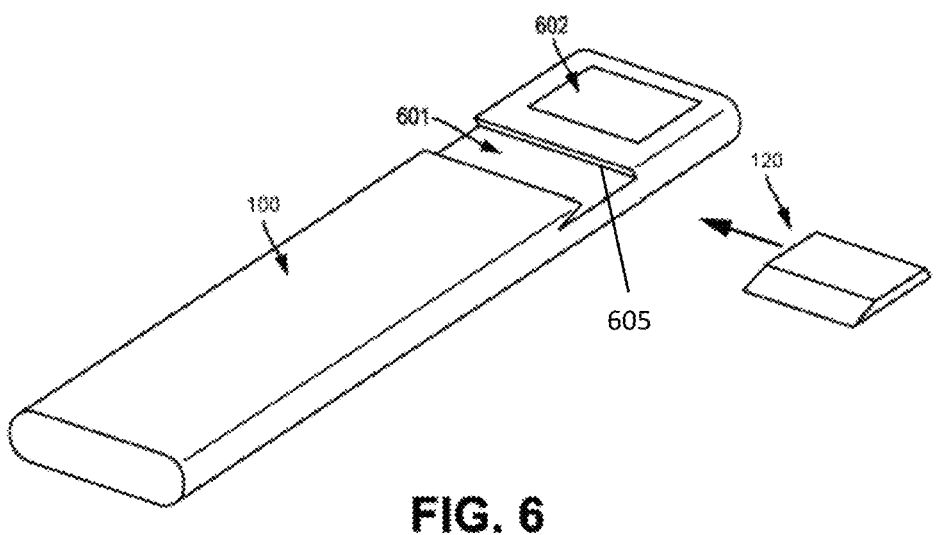
FIG. 6 illustrates a vaporizer device with a vaporizer cartridge inserted from the side, below the mouthpiece.

FIG. 6 illustrates another example of the vaporizer device 100 with a vaporizer cartridge channel 601, below (e.g., inferior to) a fingerprint or lip sensor 602. The vaporizer cartridge 120 may be laterally inserted into the vaporizer device 100 based on a size and shape of the channel 601 and the size and shape of the cartridge 120. The channel 601 and/or the vaporizer 100 may include retention features 605 to secure the vaporizer cartridge 120 within the channel 601. Once in place, the vaporizer cartridge 120 may align with the vaporizer cartridge channel 601 to deliver vapor to the user based on a reading from the sensor 602. For example, the sensor 602 may be located proximate to a mouthpiece of the vaporizer 100 such that during inhalation, the user's lip and/or finger may contact the sensor 602.

Figure 7A:
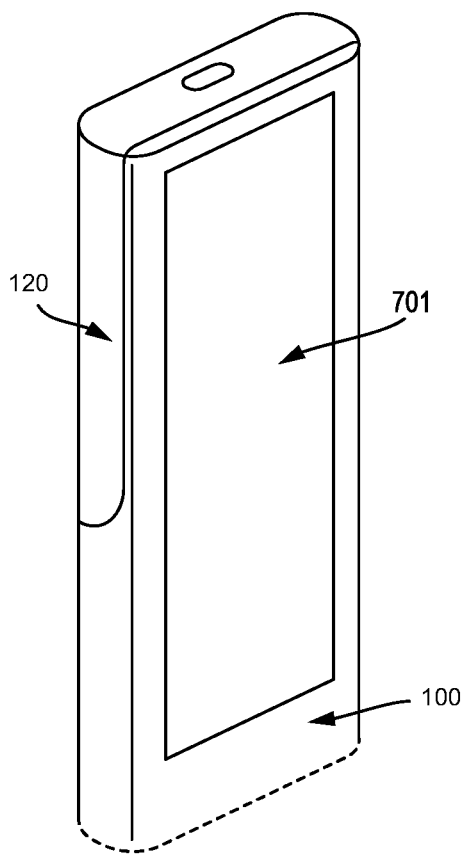
FIG. 7A illustrates a perspective view of a vaporizer device with a display module covering a portion of the face.

FIG. 7A illustrates a perspective view of another example of the vaporizer 100 having a display module 701 covering a portion of the vaporizer 100. The display module 701 may allow whole areas to be used for differentiating biological tissue. For example, the display module 701 may be configured detect a user's fingerprint and/or lip print, depending on where the user contacts the display module 701. The display module 701 may be communicatively coupled to a sensor (e.g., sensor 504) to capture the user's lip print and/or fingerprint. As shown, the vaporizer cartridge 120 may be coupled to the vaporizer 100 on an opposite side of the display module 701.

Figure 7B:
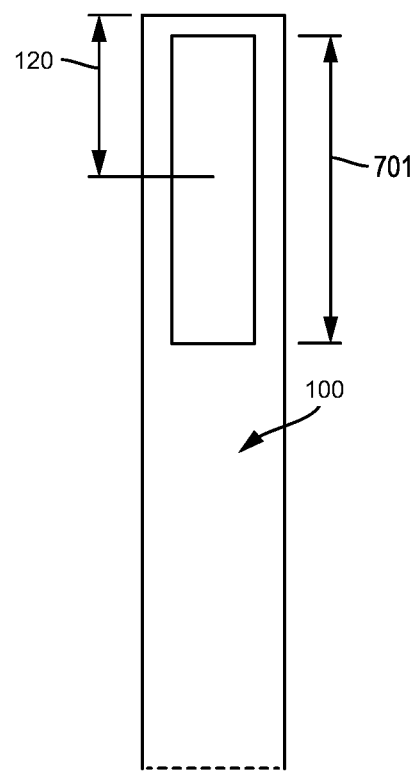
FIG. 7B illustrates a front view of a vaporizer device of FIG. 7A.

FIG. 7B illustrates a front view of the example of the vaporizer 100 shown in FIG. 7A. As shown in FIG. 7B, the vaporizer cartridge 120 may take up a portion of a back side of the vaporizer 100 (e.g., a dorsal side). The display module 701 may cover a portion of a front side (e.g., a ventral side) of the vaporizer 100. As shown, the display module 701 portion may be larger than the portion for the vaporizer cartridge 120, although other sizes are possible.

FIG. 8A illustrates another example of the vaporizer 100 with the vaporizer cartridge 120 inserted on one side of the vaporizer 100 and a sensor 802 embedded in a surface on an opposite side of the vaporizer 100. The sensor 802 may be a lip print or fingerprint sensor configured to capture an image of a user's lip or finger contacting the sensor 802. In some aspects, a mouthpiece of the vaporizer cartridge 120 may be located proximate to the sensor 802 so that a user's fingers or lips 803 may contact the sensor 802. Moreover, when a user attempts to inhale, the vaporizer 100 may unlock for use in response to lip print and/or a fingerprint detected by the sensor 802 matching an authorized user's lip print or fingerprint.

FIG. 8B illustrates the example of the vaporizer 100 shown in FIG. 8A decoupled from the vaporizer cartridge 120, showing a visible sensor 804 of the vaporizer device 800. The sensor 804 may be configured to detect and/or capture a lip print or a fingerprint of a user contacting the sensor 802.

FIG. 8C illustrates a side view of the vaporizer device 800 of FIG. 8A. As shown, the vaporizer cartridge 120 is inserted on one side of the vaporizer device 800, with an opposite side having the lip print or fingerprint sensor 802. The cartridge 120 may be configured and shaped to slide over the sensor 804 of FIG. 8B and sit flush with an end of the vaporizer 100 when the cartridge 120 is coupled with the vaporizer 100.

Figure 9A:
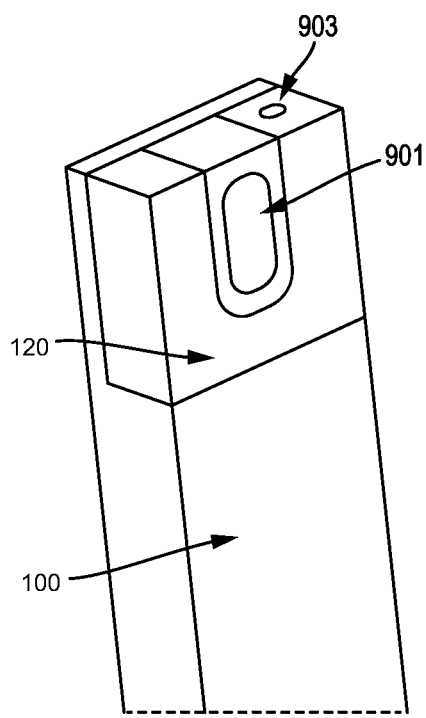
FIG. 9A illustrates a vaporizer device with an inserted U-shaped vaporizer cartridge.

FIG. 9A illustrates another example of the vaporizer 100 coupled with an example of a U-shaped vaporizer cartridge 120. A fingerprint sensor 901 may be integrated into the vaporizer 100, and situated proximate to a site of inhalation 903 (e.g., mouthpiece 130). In the example of FIG. 9A, the shape of the vaporizer cartridge 120 may allow the sensor 901 to be integrated in the vaporizer 100 rather than the vaporizer cartridge 120. For example, the vaporizer cartridge 120 may be sized and shaped to fit over and/or mate with the sensor 901. The sensor 901 may be located proximate to the site of inhalation 903 and may be configured to detect and/or capture a lip print and/or a fingerprint of the user of the vaporizer 100. In some implementations of the current subject matter, the vaporizer cartridge 120 may be disposable, for example, when the vaporizable material 102 included in the vaporizer cartridge 120 is depleted, while the vaporizer 100 remains reusable. As such, including the sensor 901 in the vaporizer 100 may reduce the complexity and cost of the vaporizer cartridge 120 as well as the amount of waste that is associated with disposing the vaporizer cartridge 120.

Figure 9B:
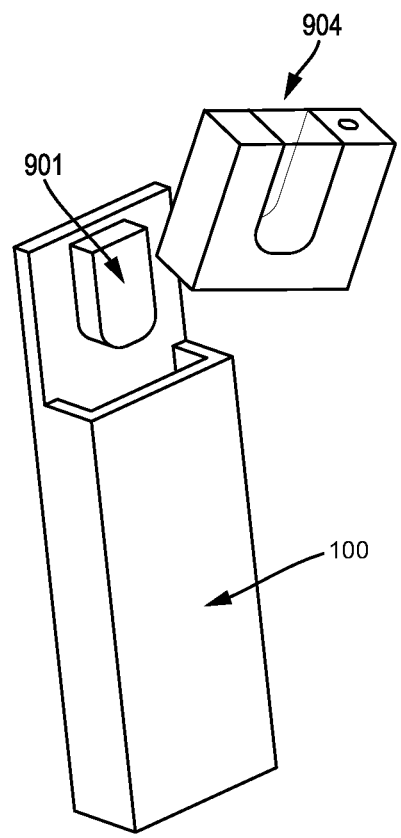
FIG. 9B illustrates a vaporizer device with a U-shaped vaporizer cartridge removed.
Figure 9C:
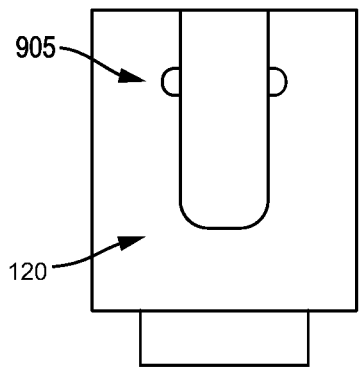
FIG. 9C illustrates a front view of a U-shaped vaporizer cartridge.
Figure 9D:
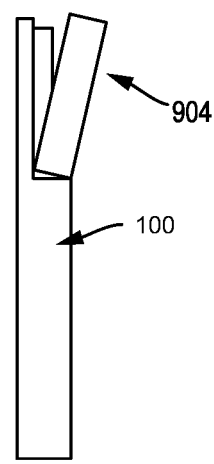
FIG. 9D illustrates a side view of a vaporizer device of FIG. 9A with a vaporizer cartridge using toe-in insertion.

FIGS. 9B and 9D depict the vaporizer 100 being coupled with the vaporizer cartridge 120 using a toe-in insertion technique 904. As shown, the toe-in insertion technique 904 may facilitate coupling of the vaporizer cartridge 120 with the sensor 901 and/or vaporizer device 100.

FIG. 9C illustrates a front view of the U-shaped vaporizer cartridge 120, which includes snap detents or springs 905 for securing the vaporizer cartridge 120 to the vaporizer 100, for example, the vaporizer body 110.

Figure 9E:
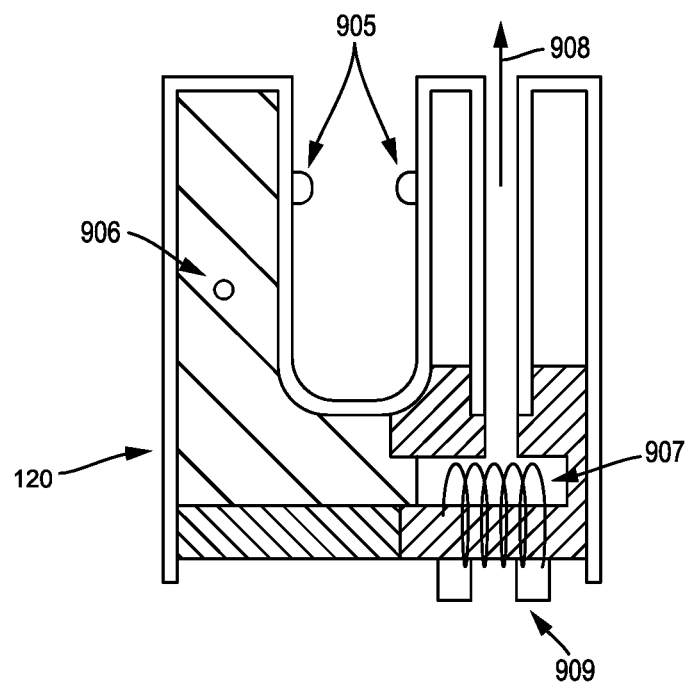
FIG. 9E illustrates an inside, cross-sectional view of a vaporizer cartridge of FIG. 9C.

FIG. 9E illustrates a front, cross-sectional view of the example of the U-shaped vaporizer cartridge 120 shown in FIG. 9C. Snap detents or springs 905 may be configured to secure the vaporizer cartridge 120 to the vaporizer 100, for example, the vaporizer body 110. The detents 905 may fit within and/or otherwise be held within the recesses of the vaporizer 100 to hold the vaporizer cartridge 120 when the vaporizer cartridge 120 is coupled with the vaporizer 100. As shown in FIG. 9E, the vaporizable material 102 may fill an interior reservoir of one column of the U-shaped vaporizer cartridge 120. As further shown in FIG. 9E, a heater and/or wick 907 may be located within the other column and may be configured to heat the vaporizable material 102 to form a vapor to be inhaled by a user through a mouthpiece and channel 908, integrated into the other column of the vaporizer cartridge 120. As further shown, the one or more cartridges contacts 124 may be located at the bottom (e.g., inferior end) of the vaporizer cartridge 120. As noted, the one or more cartridge contacts 124 may be configured to couple with the one or more receptacle contacts 125 in the vaporizer device 100 to form an electrical circuit for delivering power to the heater and/or wick 907 to heat the vaporizable material 102 to a sufficient temperature to generate an inhalable aerosol.

Figure 10A:
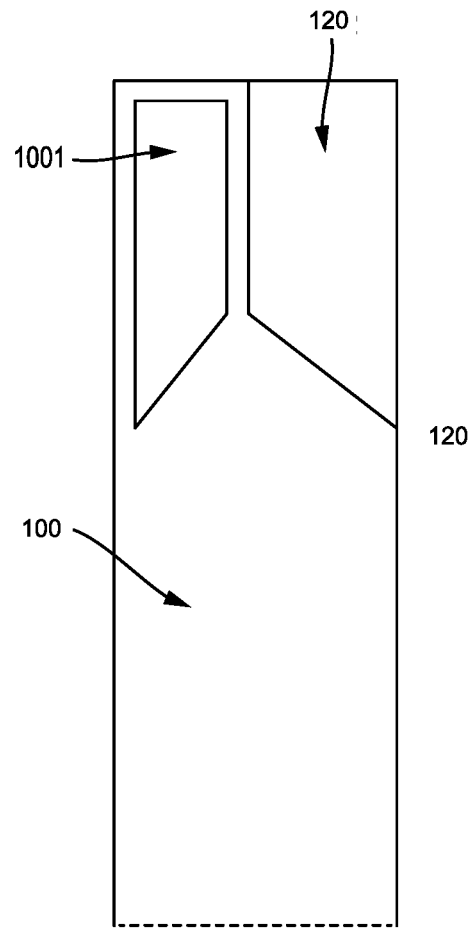
FIG. 10A illustrates a vaporizer device with a vaporizer cartridge and a sensor on the same proximal face.

FIG. 10A illustrates another example of the vaporizer 100 with a fingerprint or lip print recognition sensor 1001 and the vaporizer cartridge 120 on a same proximal face of the vaporizer 100.

Figure 10B:
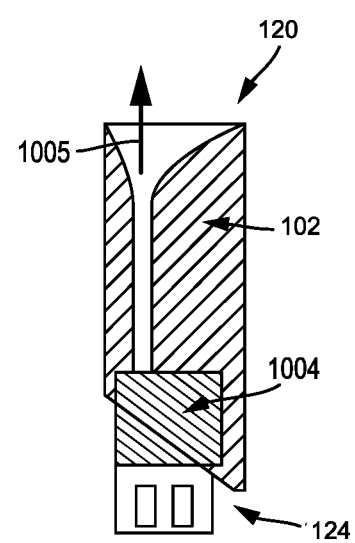
FIG. 10B illustrates an inside, cross sectional view of a vaporizer cartridge to be used with a vaporizer device of FIG. 10A.

FIG. 10B illustrates an interior, cross sectional view of an example of the vaporizer cartridge 120 to be used with the example of the vaporizer 100 shown in FIG. 10A. As shown, the vaporizable material 102 may fill the reservoir 140 of the vaporizer cartridge 120. A heater and/or wick 1004 located at an inferior end of the vaporizer cartridge 120 may be configured to heat the vaporizable material 102 to a temperature sufficient for forming vapor to be inhaled through a mouthpiece and a channel 1005 located at a superior end of the vaporizer cartridge 120. The one or more cartridge contacts 124 may be located at the bottom (e.g., the inferior end) of the vaporizer cartridge 120. The one or more cartridge contacts 124 may couple with the one or more receptacle contacts 125 to complete an electrical circuit for delivering power to the heater and/or wick 1004. In some aspects, power delivered to the heater and/or wick 1004 may be conditioned on identification, authentication, and/or authorization of the user based on a biometric data (e.g., a lip print, a fingerprint, or the like) obtained by the sensor 1001.

Figure 11:
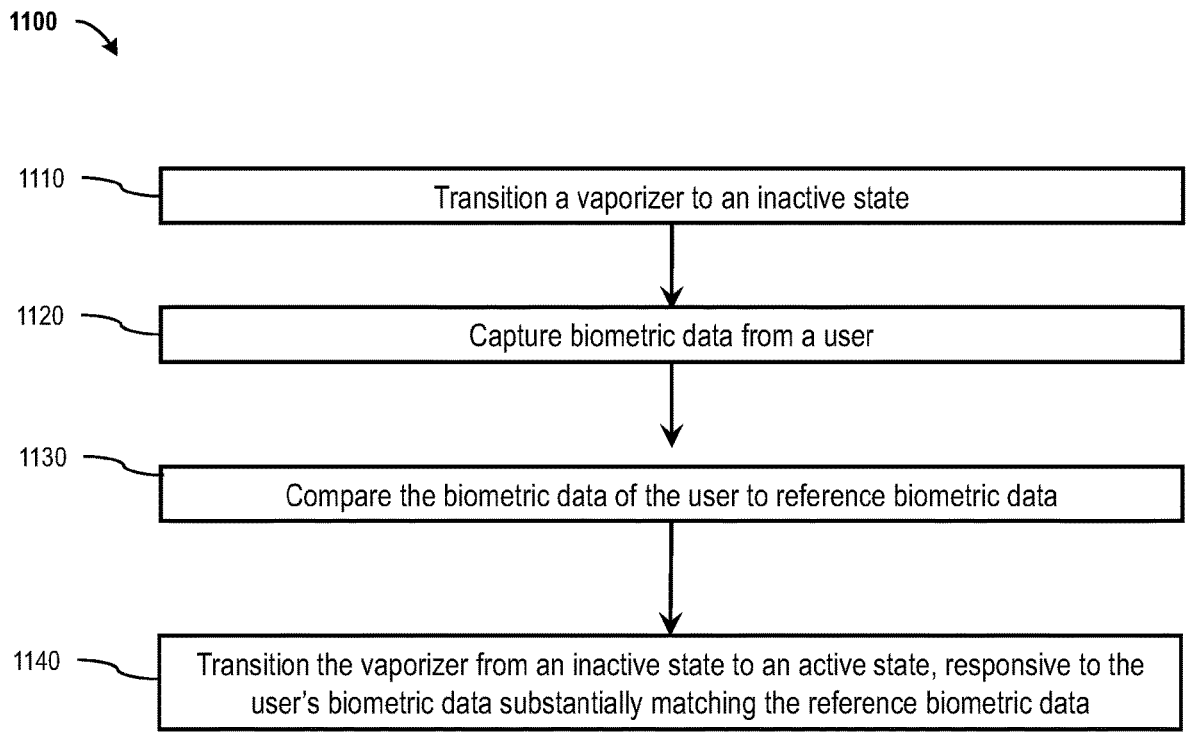
FIG. 11 illustrates a flowchart of an example method for authenticating a user of a vaporizer, in accordance with some example implementations.

FIG. 11 depicts a flowchart illustrating an example of a method 1100 for authenticating a user of a vaporizer, in accordance with some example implementations. In various implementations, the method 1100 (or at least a portion thereof) may be performed by the vaporizer 100, for example, the controller 104, a server, a computing apparatus, other related apparatuses, and/or some portion thereof.

At operational block 1110, the controller 104 may transition the vaporizer 100 to an inactive state in which the vaporizer 100 is incapable of vaporizing the vaporizable material 102 included in the vaporizer cartridge 120. For example, prior to a first use of the vaporizer 100, the vaporizer 100 may be locked in an inactive state to prevent use of the vaporizer 100. Alternatively and/or additionally, the vaporizer 100 may transition from an active state to an inactive state in response to the removal and/or insertion of the vaporizer cartridge 120, a period of inactivity more than a threshold length of time, a failed authorization, and/or the like.

At operational block 1120 the vaporizer 100, for example, can read biometric data from a user. For example, a user's lip and/or the user's finger may contact a surface of the vaporizer 100 (e.g., translucent surface 201) such as when a user attempts to inhale. At least a portion of a user's lips (e.g., lips 302) may contact the translucent surface 201. In response to detecting contact of the translucent surface 201, a sensor (e.g., sensor 203) may capture the biometric data (e.g., an image of the user's lip print or fingerprint). The sensor 203 may be coupled to a light pipe 202 configured to transmit light between the translucent surface 201 and the sensor 203.

At operational block 1130 the vaporizer 100 may compare the biometric data read from the user to reference biometric data. For example, in response to capturing biometric data from the user (e.g., an image of the user's lip print or fingerprint), a processor (e.g., controller 104) may compare the biometric data to reference biometric data. The reference biometric data may be obtained during a registration process of the vaporizer. For example, prior to a first use of the vaporizer, a user may be asked to verify his or her identity, age, purchase, location, or the like. The user may enter his or her information via a user interface associated with the vaporizer or the information may be obtained from an external server or database (e.g., DMV server). The user may provide the reference biometric data to the user interface. For example, the user may submit a sample lip print or fingerprint during the registration process to be used as the reference biometric data for later authentication and use of the vaporizer.

At operational block 1140 the vaporizer 100 may transition the vaporizer from an inactive state to an active state, responsive to the user's biometric data substantially matching the reference biometric data. The user may be previously associated with the vaporizer 100 and may be authorized to use the vaporizer 100. For example, upon the determination that the user's biometric data (e.g., the user's lip print or the user's fingerprint) matches the reference biometric data (e.g., the reference lip print or the reference fingerprint), the user may become authorized to use the vaporizer 100. In some implementations, transitioning the vaporizer 100 to the active state may be based on an age of the user. The vaporizer may determine the age or receive a determination of the age from a server and/or an application. The age of the user may be authenticated during the registration process or may be re-authenticated in response to the comparing, or at another time.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A vaporizer device, comprising:
   a sensor configured to detect biometric data; and
   a controller configured to:
      determine, based on the biometric data detected by the sensor, whether a user is authorized to use the vaporizer device, and
      in response to determining that the user is authorized to use the vaporizer device, transition the vaporizer device to an active state in which the vaporizer device is capable of vaporizing a vaporizable material, the vaporizer device being configured to enable a delivery of power from a power source to a heating element, the delivery of power to the heating element vaporizing the vaporizable material included in a vaporizer cartridge to generate an aerosol,
   wherein the sensor is integrated with a vaporizer body, the sensor shaped to mate with the vaporizer cartridge containing the vaporizable material.

2. The vaporizer device of claim 1, wherein the vaporizer device further includes the vaporizer body configured to couple to the vaporizer cartridge.

3. The vaporizer device of claim 2, wherein the vaporizer body comprises a curved surface for improved contact with the user during use of the vaporizer device, and wherein the sensor is configured to detect the biometric data via the curved surface.

4. The vaporizer device of claim 2, wherein the vaporizer body includes a cartridge receptacle configured to receive the vaporizer cartridge, and wherein the cartridge receptacle is disposed on a first side of the vaporizer body, and the sensor is disposed on a second side of the vaporizer body opposite the first side.

5. The vaporizer device of claim 4, wherein the cartridge receptacle comprises a channel on a side of the vaporizer body, wherein the vaporizer cartridge is sized and shaped to be laterally inserted into the channel, and wherein the cartridge receptacle includes retention features configured to secure the vaporizer cartridge to the vaporizer body.

6. The vaporizer device of claim 5, wherein the vaporizer cartridge is U-shaped, and wherein the sensor is proximate to the cartridge receptacle and an end of the vaporizer body, the cartridge receptacle and sensor shaped to receive and mate with the vaporizer cartridge.

7. The vaporizer device of claim 6, wherein the vaporizer cartridge comprises:
- a first portion holding the vaporizable material;
- a second portion including a wick and a heater; and
- a third portion spaced apart from the first portion by the second portion, the third portion being positioned approximately parallel to the first portion, the first portion and the third portion being positioned approximately perpendicular to the second portion, and an inner surface of the first portion and an inner surface of the third portion comprising a retention feature configured to secure the vaporizer cartridge to the vaporizer body.

8. The vaporizer device of claim 2, wherein the sensor is disposed on one side of the vaporizer body, and wherein the vaporizer cartridge is disposed over the sensor when the vaporizer cartridge is coupled to the vaporizer body.

9. The vaporizer device of claim 1, wherein the sensor comprises an optical sensor configured to capture an image of a lip and/or a finger of the user.

10. The vaporizer device of claim 9, wherein the optical sensor comprises an infrared camera.

11. The vaporizer device of claim 1, wherein the controller is configured to determine whether the user is authorized to use the vaporizer device by at least comparing the biometric data detected by the sensor to reference biometric data of a user authorized to use the vaporizer device.

12. The vaporizer device of claim 1, wherein the sensor is coupled, by a corridor, to one or more translucent surfaces on the vaporizer body and/or the vaporizer cartridge.

13. The vaporizer device of claim 12, wherein the one or more translucent surfaces include a first translucent surface and a second translucent surface, wherein the first translucent surface configured to capture a first portion of a lip print, and wherein the second translucent surface is configured to capture a second portion of the lip print.

14. The vaporizer device of claim 12, wherein the sensor is configured to detect the biometric data in response to a coverage on the one or more translucent surfaces exceeding a threshold value.

15. The vaporizer device of claim 12, wherein the sensor further comprises at least one light emitting diode configured to illuminate the corridor.

16. The vaporizer device of claim 2, wherein the sensor is integrated within the vaporizer body proximate to a display module comprising a biometric sensor configured to recognize a presence of a lip print or a fingerprint.

17. The vaporizer device of claim 1, wherein the sensor is configured to detect the biometric data in response to a pressure sensor in the vaporizer device detecting a pressure drop.

18. The vaporizer device of claim 1, wherein the sensor is configured to detect the biometric data in response to an accelerometer in the vaporizer device detecting a change in an orientation of the vaporizer device.

19. A method for identifying a user of a vaporizer device based on a biometric recognition system, the method comprising:
- transitioning, by a processor, the vaporizer device to an inactive state;
- capturing, by a sensor of the vaporizer device, biometric data of a user, wherein the sensor is integrated with a vaporizer body, the sensor shaped to mate with the vaporizer cartridge containing a vaporizable material;
- comparing the biometric data of the user to reference biometric data; and
- transitioning, in response to the comparing and in response to determining that the user is authorized to use the vaporizer device, the vaporizer device to an active state in which the vaporizer device is capable of vaporizing the vaporizable material.

20. A system for biometric recognition of a vaporizer device, the system comprising:
- at least one processor; and
- at least one memory storing instructions which, when executed by the at least one processor, cause operations comprising:
- transitioning the vaporizer device to an inactive state;
- acquiring biometric data of a user by a sensor, wherein the sensor is integrated with a vaporizer body, the sensor shaped to mate with the vaporizer cartridge containing a vaporizable material;
- comparing the biometric data of the user to reference biometric data; and
- transitioning, in response to the comparing and in response to determining that the user is authorized to use the vaporizer device, the vaporizer device to an active state in which the vaporizer device is capable of vaporizing the vaporizable material.

* * * * *